United States Patent [19]
Wipfelder et al.

[11] Patent Number: 5,811,486
[45] Date of Patent: Sep. 22, 1998

[54] REACTION RESIN SYSTEM WITH PHOSPHOROUS-CONTAINING CONSTITUENT

[75] Inventors: Ernst Wipfelder, München; Windfried Plundrich, Germering, both of Germany

[73] Assignee: Siemens Aktiengesellschaft, Munich, Germany

[21] Appl. No.: 875,320

[22] PCT Filed: Jan. 2, 1996

[86] PCT No.: PCT/DE96/00003

§ 371 Date: Jul. 25, 1997

§ 102(e) Date: Jul. 25, 1997

[87] PCT Pub. No.: WO96/23018

PCT Pub. Date: Aug. 1, 1996

[30] Foreign Application Priority Data

Jan. 26, 1995 [DE] Germany .................. 195 02 410.9

[51] Int. Cl.$^6$ .......................... C08G 65/08; C08G 65/14; C08G 59/40
[52] U.S. Cl. .................. 524/612; 525/507; 528/87; 528/103; 528/104; 528/108; 528/398
[58] Field of Search ............................ 524/612; 525/507; 528/87, 103, 104, 108, 398

[56] References Cited

U.S. PATENT DOCUMENTS

| | | | |
|---|---|---|---|
| 3,373,231 | 3/1968 | Cherbuliez et al. | 558/216 |
| 5,262,456 | 11/1993 | Wipfelder et al. | 523/457 |
| 5,587,243 | 12/1996 | Von Gentzow et al. | 528/103 |
| 5,624,979 | 4/1997 | Kleiner et al. | 528/104 |

FOREIGN PATENT DOCUMENTS

| | | |
|---|---|---|
| 0 412 425 A1 | 1/1990 | European Pat. Off. . |
| 0 451 101 A2 | 3/1991 | European Pat. Off. . |
| 1.503.429 | 8/1966 | France . |
| 475 296 | 12/1964 | Switzerland . |

*Primary Examiner*—Kriellion S. Morgan
*Attorney, Agent, or Firm*—Hill & Simpson

[57] ABSTRACT

For better flame-retardant finishing and better workability of an epoxy-anhydride reaction resin system, it is proposed to supplement the reaction resin system with phosphonic semi-ester as additional reactive constituents. These are produced by conversion of phosphonic acid anhydride with single-valent or multi-valent alcohols. As a result of the selection of the alcohol constituent, property features of the molding material modified therewith that are already advantageous can be designationally set without thereby negatively influencing the hardening characteristic. Even with slight parts of phosphonic acid semi-ester, shaped members manufactured therefrom exhibit an adequate flame-retardant behavior given an otherwise unmodified property profile.

15 Claims, No Drawings

REACTION RESIN SYSTEM WITH PHOSPHOROUS-CONTAINING CONSTITUENT

The present invention relates generally to flame-retardant materials for covering and enveloping electrical and electronic components. More specifically, the present invention relates to flame-retardant reaction resin molding materials that are useful for serving as casings and coverings for electrical and electronic components.

Flame-retardant reaction resin molding materials that are reliable to process are required for covering and enveloping electrical and electronic components. Particularly given passive components, reaction resins that can be processed by casting are thereby standard. Epoxy resins that can be highly thermally stressed and thereby exhibit good mechanical and electrical properties are employed therefor to a great extent. The low-molecular or, respectively, oligomeric initial constituents can be converted to high-quality duroplastic materials upon employment of a great range of hardening agents such as, for example, carboxylic acid anhydrides, amines, phenols or isocyanate or, respectively, by ionic polymerization. The low-molecular through oligomeric initial condition of the epoxy resins is responsible for the advantageous processing behavior of epoxy resins. They can be highly filled with inorganic, inert fillers and can still be processed as casting resin even then.

The flame-retardant finishing of epoxy resin molding materials is currently generally accomplished with halogen-containing and specific bromine-containing aromatic constituents. These embedded constituents, which frequently contain antimony trioxide as a synergist, however, present additional problems in the case of a fire. Given carbonization or combustion, they release decomposition products that are corrosive and, under unbeneficial conditions, ecologically and toxicologically suspect. A substantial technical outlay, moreover, must also be exerted for risk-free waste disposal by incineration.

Phosphorous-containing additives for epoxy resins that improve the flame-retardancy have been recently disclosed. U.S. Pat. No. 5,262,456 proposes that a phosphinic acid or, respectively, phosphonic acid derivative be bonded with alcoholic hydroxyl groups in an epoxy resin molding material. DE 42 37 132 discloses employing phosphorous constituents on a phosphine oxide or, respectively, phosphonate basis as a reaction resin constituent for increasing flame-retardancy. DE 43 08 185 A1 discloses that polyepoxy compounds be converted into phosphorous-containing epoxy compounds by conversion with a phosphonic acid anhydride and that these epoxy compounds then be crosslinked with known hardener constituents into flame-retardant molding materials.

A shared disadvantage of these phosphorous compounds, however, is their relatively low phosphorous content. As a consequence thereof, substantial quantities of these phosphorous-containing compounds are required in order to obtain a satisfactory flame-retardancy. Clear limitations in the workability of such modified reaction resin systems thereby derive because of the high viscosity of these phosphorous constituents particularly observed given phosphorous-modified epoxy resins. The phosphonic acid derivatives are in fact usually lower in viscosity and can thus be advantageously utilized for casting technology. However, the exhibit a weaker flame-retardant effect and must therefore be utilized in higher concentration, which can in turn negatively influence the molding material properties.

SUMMARY OF THE INVENTION

It is therefore an object of the present invention to modify a reaction resin system on an epoxy resin basis such that a molding material manufactured therefrom meets the flame-retardant specifications demanded for electronic components, without negatively affecting the workability of the reaction resin system, the molding material properties or the dependability of a component covered or enveloped with the molding material, and such that the molding material does not produce and eco-toxicologically harmful decomposition products when burned.

The invention is based on the discovery of semi-esters of phosphonic acid with alcohols. Surprisingly, these phosphorous-containing compounds i.e. the conversion product of phosphonic acid anhydride and a compound with at least one alcoholic OH group can be mixed in any proportion with the other constituents which include an epoxy resin constituent and a carboxylic acid anhydride of a known reaction resin system. It is thereby possible to add the conversion product of phosphonic acid anhydride and a compound with at least one alcoholic OH group to the reaction resin mass either directly or, especially advantageously, mixed with standard, in particular liquid carboxylic acid anhydrides.

It is also possible to provide the conversion product of phosphonic acid anhydride and the alcohol as the sole hardener component.

Therefore, in an embodiment, the reaction resin system of the present invention comprises an epoxy resin and a hardener which is a conversion product of a phosphonic acid anhydride and an alcohol having at least two OH groups. The phosphonic acid group comprises a radical selected from the group consisting of an alkyl radical having from 1 to 40 carbon atoms, an alkylene radical having from 1 to 40 carbon atoms, a cycloaliphatic radical and an aryl radical.

In an embodiment, the resin system of the present invention has a phosphorous content ranging from about 1% to about 10% by weight.

In an embodiment, the alcohol further comprises a linear, branched cyclic multi-valance alcohol selected from the group consisting of alkanol, alkenol and corresponding aromatically substituted derivatives of alkanol and alkenol.

In an embodiment, the resin system of the present invention further comprises additives selected from the group consisting of reaction accellerants, reactive dilutants, filler, flow improvers or viscosity reducers, adhesion promoters, thixotroping agents, colorants and pigments.

In an embodiment, the alcohol comprises phosphorous.

In an embodiment, the alcohol is selected from the group consisting of hydroxyalkyl-substituted phosphine oxide, hydroxylalkyl-substituted phosphine, phosphone and phosphoric acid ester containing hydroxyl groups.

In an embodiment, the hardener of the resin system of the present invention further comprises carboxylic acid anhydride.

In an embodiment, the resin system of the present invention has a viscosity of less than 10,000 mPAS at typical casting conditions.

In an embodiment, the present invention provides a method of manufacturing a phosphorous-containing reaction resin system that comprises the steps of producing a hardener as a conversion product of a phosphonic acid anhydride and an alcohol in an inert solvent, removing the hardener from the solvent and combining the hardener with an epoxy resin to form a reaction resin system.

In an embodiment, the production of the hardener is carried out at room temperature.

In an embodiment, the producing of the hardener further comprises mixing a carboxylic acid anhydride with the phosphonic acid anhydride and the alcohol.

Other objects and advantages of the present invention will become apparent upon reading the following detailed description and appended claims, and upon reference to the accompanying drawings.

DETAILED DESCRIPTION OF THE PRESENTLY PREFERRED EMBODIMENTS

As a result of the variety in the selection of the alcohol constituent for the phosphorous-containing conversion product of phosphonic acid anhydride and a compound with at least one alcoholic OH group, it is possible to designationally set the mechanical, thermal, electrical and chemical properties of a molding material produced therefrom without disadvantageously influencing the hardening characteristic of the inventive reaction resin system. Surprisingly, it was found that such phosphorous-containing semi-esters behave like carboxyl-functional acid ester with respect to hardenability. Over and above this, such phosphorous-containing semi-esters are easily worked, low-viscosity liquids that usually exhibit a high phosphorous content. A phosphorous content of 15.7 percent be weight is provided by for the conversion product of, for example, propane phosphonic acid anhydride and 1,5-pentanediol. For this reason, only small quantities of the phosphorous-containing conversion product are required in order to effect an adequate flame-retardancy. Table 1 shows the most important characteristics of this semi-ester. In addition, the part of the phosphorous-containing semi-ester for realizing an adequately flame-retardant molding material is listed. For a relatively high phosphorous content of 3 percent by weight in the casting resin system, for example, only 16 percent by weight semi-ester are thus required.

TABLE 1

| Characteristics of a Semi-Ester of Propane Phosphonic Acid Anhydride and 1,5-Pentanediol | |
|---|---|
| Conversion Product | Propane Phosphonic Acid Anhydride (PPA)/1,5-Pentanediol |
| Mol ratio | 2.0:1.0 |
| Phosphorous content | 19 |
| Acid value mol/100 g | |
| theoretical | 0.63 |
| found | 0.65 |
| Viscosity mPas at | |
| 25° C. | 3040 |
| 60° C. | 540 |
| 80° C. | 260 |
| Storage stability months at RT | >12 |
| Semi-ester part % | 16 |

With the invention, thus, it is possible to modify an arbitrary reaction resin system on an epoxy/anhydride basis in the direction of improved flame-retardancy. The known reaction resin system can thereby comprise properties optimized in view of a specific use that are not deteriorated by the inventive modification (addition of the phosphorous-containing semi-ester).

An adequately high flame-retardancy is achieved given a phosphorous content of the reaction resin system of 1 to 5 percent by weight. As in the case of known, phosphorous-free reaction resin systems, the reactivity of such phosphorous-modified reaction resin systems can be designationally set by the addition of accelerants.

The viscosity of the inventive reaction resin system, which can be set low, makes a higher filler content possible; the filler content can comprise up to 70 percent by weight for a casting resin application.

However, it is not only the phosphorous content that is of significance for the flame-retardant properties of the inventive reaction resin system or, respectively, the molding material produced therefrom; rather, the carboxylic acid anhydride is also of significance. Further improvements in the flame-retardancy are achieved when the anhydride is derived from an aromatic di- or tetra-carboxylic acid. The aromatic framework of the carboxylic acid can thereby be a single-nucleus or multi-nucleus aromatic. Phthalic acid anhydride represents the simplest species of this group of compounds.

Further examples of suitable aromatic anhydrides are benzene-1,2,4,5-tetracarboxylic acid anhydride, benzophenone tetracarboxylic acid anhydride or perylene-3,4,9,10-tetracarboxylicacid-3,4,9,10-dianhydride, naphthalene-1,8-dicarboxylic acid anhydride, benzoic acid anhydride or biphenyltetracarboxylic acid dianhydride.

In addition to the aromatic anhydrides, cycloaliphatic, aliphatic and olefinic anhydrides are utilized, such as, for example, hexahydrophthalic acid anhydride, methylhexahydrophthalic acid anhydride, succinic acid anhydride, valeric acid anhydride, isovaleric acid anhydride, hexane acid anhydride, pivalic acid anhydride, 5-norbornene-2,3-dicarboxylic acid anhydride, maleic acid anhydride, 2-dodecene-1-yl-succinic acid anhydride and methyltetrahydrophthalic acid anhydride.

A commercially available epoxy resin or a mixture of commercially available epoxy resins can be selected as epoxy resin constituent (component A). The polyglycidylethers on a basis of bisphenol-A and bisphenol-F have thereby proven especially advantageous. In addition to the especially suitable aromatic polyglycidylethers, those of aliphatic alcohols are also suitable. Let 1,4-butanediol, 1,6 hexanediol, polyalkyleneglycols, glycerine, trimethylpropane, bis-(4-hydroxycyclohexl)-2,2-propane and pentaerythrite be cited as example of such multi-valent alcohols.

Polyglycidylesters are also suitable that are obtained by conversion of, for example, epichlorohydrin or similar epoxy compounds with aliphatic, cycloaliphatic or aromatic polycarboxylic acids. Further, polyepoxys that are obtained epoxification of polyalkenes are also suitable for the epoxy constituent.

The alcohol constituent in the inventive reaction resin system can be a linear, branched or cyclic single-valent or multi-valent alcohol. It can be selected from alkanol, alkenol and corresponding, aromatically substituted derivatives.

Compounds with phenolic OH groups are not suitable as the alcohol component.

Primary aliphatic di- or polyols are preferred. The conversion with multi-valent alcohols has the advantage that semi-esters with a high relative phosphorous content thus arise since every alcoholic hydroxyl group is capable of forming a phosphonic acid semi-ester with phosphonic acid anhydride.

For example, single-valent alcohols of propanol through hexadecanol are suitable alcohol constituents. Suitable unsaturated alcohols are, for example, allylalcohol, propargyl alcohol and others. Well-suited diols extend from glycol via pentadiol to decandiol.

For example, bisphenol-A-bis(hydroxyethylether) is a suitable aromatically substituted alcohol.

Multi-valent alcohols are, for example, pentaerythrite or :trimethyololpropane.

Longer-chained or oligomeric through polymeric alcohols have a flexibilizing effect in the inventive reaction resin system. Such oligomeric through polymeric alcohols can be polyetherpolyols, polyesterpolyols or polyesteretherpolyols.

Cyclic or polycyclic alcohols as the alcohol constituent can improve the thermally mechanically properties of the reaction resin system or, respectively, of the molding material produced therefrom. Let only the TCD alcohol deriving from cyclopentadiene chemistry be representative.

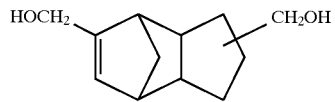

In view of a further increase in the phosphorous content in the reaction resin system, phosphorous-containing alcohols can also be advantageously utilized as constituent D for the production of the phosphonic acid semi-ester (i.e. the conversion product of phosphonic acid anhydride and the alcohol constituent).

Such alcohols can also be selected from hydroxyalkyl-substituted phosphine, phosphonic and phosphoric acid esters. Compounds that are suitable and readily available are, for example, sec. butyl-bis(3-hydroxypropyl)-phosphineoxide, diethyl-N,N-bis(2-hydroxyehtyl) aminomethyl phosphonate, 2-hydroxyethane phosphane acid dimethyl ether or tris-(hydroxymethyl)-phosphinic acid. Table 2 shows the significant characteristics of the semi-ester of propanephosphonic acid anhydride and sec. butyl-bis-(3-hydroxypropyl)-phosphinic oxide.

TABLE 2

Characteristics of the Semi-Ester of Propane Phosphonic Acid Anhydride and sec. butyl-bis-(3-hydroxypropyl)-phosphinic oxide.

| Conversion Product | Propane Phosphonic Acid Anhydride (PPA/sec. butyl-bis-(3-hydroxypropyl)-phosphinic oxide (FRD) |
|---|---|
| Mol ratio | 1.9:1.0 |
| Phosphorous content | 20 |
| Acid value mol/100 g | |
| theoretical | 0.68 |
| found | 0.64 |
| Viscosity mPas | |
| 60° C. | 16000 |
| 80° C. | 4320 |
| Storage stability months at RT | >12 |

Since the invention is directed to the modification of a traditional epoxy/anhydride reaction resin system, additional additives can be contained in the inventive reaction resin system. These are known additives for epoxy resins that influence the workability, the color or the properties of the hardened molding material and that can be selected dependent on the desired application.

Such additives can be: reaction accelerants, reaction dilutants, flow improvers, defoaming agents, adhesion promoters, thixotroping agents, colorants, pigments and, in particular, fillers. In addition to an improvement of the thermally mechanical properties, the flame resistance can be additionally increased by fillers. Even though this is already achieved with a high filler content and, thus, a diminution of the part of the organic resin matrix, the flame-retardancy can also be improved by the selection of the filler. For example, aluminum hydroxide is a filler with flame-retardant property that has good compatibility with the inventive reaction system.

For producing the phosphonic acid semi-ester, phosphonic acid anhydride

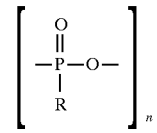

and
a compound having at least one alcoholic OH group are converted with one another in substance or in an inert solvent. Preferably, a phosphonic acid anhydride solution is slowly added at room temperature and upon moisture exclusion drop by drop to the alcohol constituent present in substance or in solution. After the end of the reaction, the solvent is withdrawn and the carboxylic acid anhydride and/or conversion product of phosphonic acid anhydride and alcohol are obtained as adducts that can be directly introduced in the reaction resin system.

The production of a phosphonic acid semi-ester from propane phosphonic acid anhydride and a phosphorous-free alcohol, for example 1.5-pentanediol, is shown in Equation (1).

Reaction Equation (1)

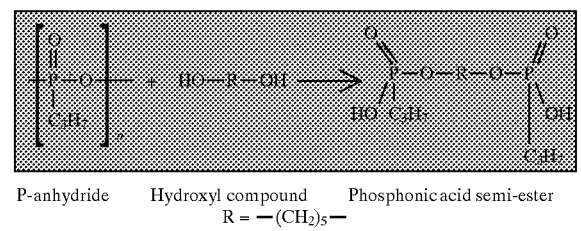

P-anhydride    Hydroxyl compound    Phosphonic acid semi-ester
$R = -(CH_2)_5-$

The production of a phosphonic acid semi-ester from propane phosphonic acid anhydride and the hydroxy-functional phosphorous compound sec. butyl-bis-(3-hydroxypropyl)phosphine oxide is shown in Equation (2).

Reaction Equation (2):

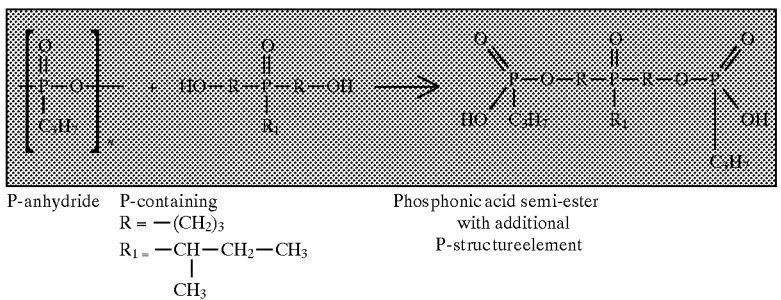

P-anhydride  P-containing  
R = —(CH$_2$)$_3$  
R$_1$ = —CH—CH$_2$—CH$_3$  
      |  
     CH$_3$ Phosphonic acid semi-ester  
with additional  
P-structureelement The invention is explained in greater detail below with reference to exemplary embodiments.

1$^{st}$ EXAMPLE

For producing the phosphonic acid semi-ester I, composed of sec. butyl-bis-(3-hydroxypropyl)-phosphine oxide (FRD) and propane phosphonic acid anhydride (PPA), 26.2 mass parts (0.118 mol) FRD and 7.0 mass parts dried ethylmethyl ketone are pre-mixed. Over 1–2 hours and upon exclusion of moisture, 47.5 mass parts of a 50% PPA solution (corresponding to 0.224 mol PPA) are added at room temperature with a drip funnel. After the end of the reaction, the solvents are quantitatively withdrawn in a rotation evaporator in a vacuum at 60°–80° C. Subsequently, the reaction mixture is treated for another hour at 120° C.

The phosphonic acid semi-ester adduct obtained exhibits a viscosity of 4300 mPas at 800° C. and yields an acid value of 0.64 mol/100 g.

2$^{nd}$ EXAMPLE

The production of the phosphonic acid semi-ester II, composed of 1.5-pentanediol (POL) and propane phosphonic acid anhydride (PPA), ensues in the same way as described in Example 1.

12.3 mass parts (0.12 mol) 1,5-pentanediol, 4.9 mass parts dried ethyl methyl ketone and 50.0 mass parts of a 50% PPA solution (corresponding to 0.24 mol PPA) are utilized.

This phosphonic acid semi-ester exhibits a phosphorous content of 19% and a viscosity of 540 mPas at 60° C. An acid value of 0.65 mol/100 g results.

Under exclusion of moisture, this phosphorous-modified adduct exhibits a storage life of over 1 year at room temperature.

3$^{rd}$ EXAMPLE 100.0 mass parts of an epoxy phenol novolak (DEN 438), 200.0 mass parts of a bisphenol=F-diglycidyl ether (P Y 306) are mixed at 80° C. with 85.0 mass parts of the phosphonic acid semi-ester I, 179.5 mass parts hexahydrophthalic acid anhydride (HHPSA) and 141.1 mass parts aluminum hydroxide (Apyral 4), degasified and then hardened for 1 hour at 110° C. and for 2 hours at 150° C. Molding materials having good mechanical, thermal and electrical properties and, in particular, flame-retardant specification according to UL 94 VO of 0.8 mm with 0.8 specimen thickness are obtained.

From the above description, it is apparent that the objects of the present invention have been achieved. While only certain embodiments have been set forth, alternative embodiments and various modifications will be apparent from the above description to those skilled in the art. These and other alternatives are considered equivalents within the spirit and scope of the present invention.

We claim:

1. An unhardened reaction resin system comprising:
   a phosphorous-free epoxy resin,
   an epoxy-free hardener comprising a conversion product of a phosphonic acid anhydride having the following structure

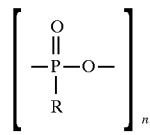

and an alcohol having at least two OH groups,
   whereby R is selected from the group consisting of an alkyl radical having 1 to 40 C atoms, an alkylene radical having 1 to 40 C atoms, a cycloaliphatic radical and an aryl radical, whereby n is a whole number,
   and the resin system having a phosphorous content ranging from about 1 percent to about 10 percent by weight.

2. The resin system of claim 1 wherein the alcohol further comprises a linear, branched of cyclic multi-valence alcohol selected from group consisting of alcanol, alkenol and corresponding aromatically substituted derivatives of alcanol and alkenol.

3. The resin system of claim 1 further comprising additives selected from the group consisting of reaction accellerants, reactive dilutants, filler, flow improvers, adhesion promoters, thixotroping agents, colorants and pigments.

4. The resin system of claim 1 wherein the alcohol comprises phosphorous.

5. The resin system claim 4 wherein the alcohol is selected from the group consisting of hydroxyalkyl-substituted phosphine oxide, hydroxyalkyl-substituted phosphine, phosphone and phosphoric acid ester containing hydroxyl groups.

6. The resin system of claim 1 wherein the hardener further comprises carboxylic acid anhydride.

7. The resin system of claim 1 wherein the resin system has a viscosity of less than 10,000 mPAS at casting conditions.

8. A hardened reaction resin system comprising:
   a phosphorous-free epoxy resin,
   an epoxy-free hardener comprising a carboxylic acid anhydride and a conversion product of a phosphonic acid anhydride having the following structure

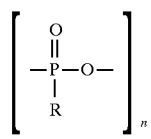

and an alcohol having at least two —OH groups, the alcohol containing phosphorus and selected from the group consisting of hydroxyalkyl-substituted phosphine oxide, hydroxyalkyl-substituted phosphine, phosphone and phosphoric acid ester containing hydroxyl groups, and whereby R is selected from the group consisting of an alkyl radical having 1 to 40 C atoms, an alkylene radical having 1 to 40 C atoms, a cycloaliphatic radical and an aryl radical, whereby n is a whole number, and the resin system having a phosphorous content ranging from about 1 percent to about 10 percent by weight.

9. The resin system of claim 8 wherein the alcohol further comprises a linear, branched of cyclic multi-valence alcohol selected from group consisting of alcanol, alkenol and corresponding aromatically substituted derivatives of alcanol and alkenol.

10. The resin system of claim 8 further comprising additives selected from the group consisting of reaction accellerants, reactive dilutants, filler, flow improvers, adhesion promoters, thixotroping agents, colorants and pigments.

11. The resin system of claim 8 wherein the hardener further comprises carboxylic acid anhydride.

12. The resin system of claim 8 wherein the resin system has a viscosity of less than 10,000 mPAS at casting conditions.

13. A method for manufacturing a phosphorous-containing reaction resin system, the method comprising the following steps:

producing an epoxy-free hardener as a conversion product of phosphonic acid anhydride and an alcohol in an inert solvent, whereby the phosphonic acid anhydride has the structure

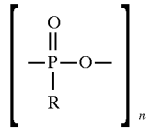

and the alcohol has at least two —OH groups and whereby R is selected from the group consisting of an alkyl radical having from 1 to 40 C atoms, an alkylene radical having from 1 to 40 C atoms, a cycloaliphatic radical and an aryl radical, and whereby n is a whole number, removing the hardener from the solvent, combining the hardener with a phosphorus-free epoxy resin to form the reaction resin system.

14. The method of claim 13, whereby the producing of the hardener is carried out at room temperature.

15. The method of claim 13 wherein the producing step further comprises mixing a carboxylic acid anhydride with the phosphonic acid anhydride and the alcohol.

* * * * *